United States Patent
Wayman et al.

(10) Patent No.: US 9,128,019 B2
(45) Date of Patent: Sep. 8, 2015

(54) PIPELINE CONDITION DETECTING METHOD AND APPARATUS

(75) Inventors: Malcolm Wayman, Northumberland (GB); Richard Treece, Northumberland (GB)

(73) Assignee: Advanced Engineering Solutions Ltd., Cramlington, Northumberland (GB)

( * ) Notice: Subject to any disclaimer, the term of this patent is extended or adjusted under 35 U.S.C. 154(b) by 1096 days.

(21) Appl. No.: 12/743,133

(22) PCT Filed: Nov. 17, 2008

(86) PCT No.: PCT/GB2008/003847
§ 371 (c)(1),
(2), (4) Date: Aug. 5, 2010

(87) PCT Pub. No.: WO2009/063218
PCT Pub. Date: May 22, 2009

(65) Prior Publication Data
US 2010/0300184 A1    Dec. 2, 2010

(30) Foreign Application Priority Data

Nov. 16, 2007  (GB) .................................. 0722534.5

(51) Int. Cl.
*G01N 17/00* (2006.01)
*G01N 17/02* (2006.01)
*F17D 5/00* (2006.01)

(52) U.S. Cl.
CPC . *G01N 17/02* (2013.01); *F17D 5/00* (2013.01)

(58) Field of Classification Search
USPC ............................................................. 73/73
See application file for complete search history.

(56) References Cited

U.S. PATENT DOCUMENTS

| | | | | |
|---|---|---|---|---|
| 1,979,912 | A | * | 11/1934 | Stirling ........................... 33/836 |
| 4,061,965 | A | * | 12/1977 | Nelson .......................... 205/730 |
| 5,030,911 | A | | 7/1991 | Lam |
| 5,451,862 | A | * | 9/1995 | Bass et al. ....................... 324/67 |
| 5,892,163 | A | | 4/1999 | Johnson |
| 6,336,983 | B1 | * | 1/2002 | Fawley ........................... 156/94 |
| 6,667,709 | B1 | | 12/2003 | Hansen et al. |
| 2001/0009372 | A1 | | 7/2001 | Kuo |
| 2003/0011363 | A1 | * | 1/2003 | Wayman et al. .............. 324/238 |

(Continued)

FOREIGN PATENT DOCUMENTS

| | | |
|---|---|---|
| DE | 4017238 | 12/1991 |
| EP | 1152235 | 11/2001 |
| EP | 1262771 | 12/2002 |

*Primary Examiner* — Robert R Raevis
(74) *Attorney, Agent, or Firm* — Gable Gotwals (57) ABSTRACT

The current invention relates to a method and apparatus for assessing the condition of a pipeline and also predicting the future rate of deterioration and/or possible failure of the pipeline. The method includes the steps of selecting at least one portion of the pipeline for which the prediction is to be made and, for that portion, monitoring or inspecting and assessing the condition of the pipeline wall, and typically also assessing the condition of any coating of the pipeline at said portion as well as the condition of the soil adjacent the pipeline. The measurement is performed along the length of the portion and preferably around the circumference of the pipeline at said portion. Data is collected for each cell of a grid which represents the said portion and on the basis of the measured data and, selectively, previous data and or reference data, an accurate prediction can be made as to the future condition of the pipeline and also identify potential future problems or required remedial works.

15 Claims, 7 Drawing Sheets (56) References Cited

U.S. PATENT DOCUMENTS

2003/0169058 A1* 9/2003 Pierre et al. .................. 324/700
2006/0288756 A1* 12/2006 De Meurechy ................ 73/1.01
2008/0036476 A1* 2/2008 Nielsen et al. ................ 324/700

* cited by examiner

| TABLE 4.2 COATING FAILURE DISTRIBUTION – PERCENTAGE COATING FAILURE ON EAST PIPE SECTION | | | | | | | | | | | | |
|---|---|---|---|---|---|---|---|---|---|---|---|---|
| | | Axial Distance from Datum Point (mm) | | | | | | | | | | % Coating failure per circumferential location |
| | | 0-100 | 100-200 | 200-300 | 300-400 | 400-500 | 500-600 | 600-700 | 700-800 | 800-900 | 900-1000 | |
| Circumferential Location | A | 30 | 40 | 50 | 50 | 40 | 40 | 60 | 50 | 30 | 60 | 45 |
| | B | 30 | 40 | 40 | 50 | 50 | 50 | 60 | 30 | 40 | 50 | 44 |
| | C | 30 | 50 | 60 | 50 | 50 | 70 | 60 | 50 | 40 | 50 | 51 |
| | D | 40 | 40 | 40 | 60 | 60 | 60 | 70 | 60 | 50 | 50 | 53 |
| | E | 40 | 60 | 60 | 50 | 70 | 60 | 60 | 40 | 60 | 60 | 57 |
| | F | 40 | 40 | 50 | 50 | 50 | 70 | 70 | 80 | 60 | 50 | 56 |
| | G | 40 | 50 | 50 | 50 | 60 | 60 | 60 | 80 | 70 | 60 | 58 |
| | H | 40 | 30 | 30 | 30 | 20 | 30 | 20 | 20 | 20 | 20 | 26 |
| | I | 20 | 20 | 20 | 20 | 10 | 10 | 10 | 20 | 10 | 10 | 15 |
| | J | 70 | 60 | 50 | 70 | 70 | 50 | 40 | 40 | 40 | 50 | 49 |
| % Coating failure per axial location | | 38 | 43 | 45 | 49 | 48 | 50 | 51 | 47 | 42 | 41 | |
| Overall area of coating failure (%) | | | | | | | | | | | | 45.4 |
| Total Cells Analysed | | | | | | | | | | | | 100 |

PIPELINE CONDITION DETECTING METHOD AND APPARATUS

CROSS-REFERENCE TO RELATED APPLICATIONS

This application is the United States National Phase of PCT Patent Application No. GB2008/003847 filed on 17 Nov. 2008, which claims priority to United Kingdom Patent Application No. 0722534.5 filed 16 Nov. 2007, both of which are incorporated herein by reference.

The invention which is the subject of this application is directed towards a method and apparatus which allows the condition of a pipeline, or predetermined length of the same, to be predicted and assessments then made as to any remedial work which may be required in a reliable and efficient manner.

The condition of pipelines which are used to carry fluids will deteriorate over time. The rate of deterioration may vary over the length of the pipeline and with respect to other conditions which may prevail on the pipeline such as the type of material carried along the pipeline and environmental conditions surrounding the pipeline.

There are many forms of apparatus which may be used to attempt to determine the condition of pipelines and one such form of apparatus is disclosed in the applicant's patent application EP 1262771. In this document there is provided apparatus and a method of identifying the presence of a defect in the pipeline and also determining whether the defect is present on the interior or exterior surfaces of the wall of the pipeline. The contents of that document are incorporated herein by reference thereto.

In order to assess the condition of a pipeline it is generally required to be able to determine the known pipe wall deterioration rates for the particular pipeline in question, the loading regimes applied to the pipeline, the drivers which may cause corrosion of the pipeline and whether or not any, and what type, of corrosion protection has been used.

The aim of the present invention is to provide a method which allows the condition of the pipeline to be determined accurately along a predetermined length of the same, without having to inspect the whole of said predetermined length. As one will appreciate, it is necessary for the method of the invention to be reliable in order to ensure that the measurements made, and the predictions made on the basis of those measurements, are accurate and reliable.

In a first aspect of the invention there is provided a method for detecting the condition of a length of pipeline, said method comprising the steps of, identifying at least one portion of the length of pipeline which is to be tested, measuring for that said portion at least the condition of the pipe wall, wherein the condition of the pipe wall is measured along the length of the portion and around at least part of the circumference of said portion of the pipeline.

Typically, when access of the apparatus is permitted and/or possible, the entire circumference of the portion of pipeline will be inspected.

In one embodiment the method includes the further step of measuring the condition of the pipeline protective coating if one is provided. In one embodiment the method includes the further step of determining the characteristics of the soil in the vicinity of the pipeline.

Typically the method includes the step of predicting the condition of the pipeline length based on the measurements taken with respect to the said portion or portions.

In one embodiment, based on the predictions, any required remedial actions can be taken at that time and/or can be scheduled for future performance.

In one embodiment, the prediction made can be determined on the basis of previously known data and measured data.

In one embodiment the portion of the pipeline which is selected is that which is regarded as being located in a critical part of the pipeline and/or located in that part of the pipeline which is regarded as being most susceptible to deterioration or most heavily loaded. Alternatively the portion or portions can be selected randomly along the length of the pipeline.

In one embodiment the number of defects in a given portion of the pipeline are determined and assessed as to whether there is a sufficient number to allow the analysis to be performed. If there is an insufficient number then the length of the portion which is assessed will be increased or alternatively the condition of the pipeline is determined to be acceptable for a period of time in the future.

In one embodiment the soil condition is determined by measuring the pH, resistivity, redox potential, ground type, moisture content and/or heterogeneity of the same.

In addition or alternatively the soil condition is determined by using apparatus comprising a plurality of electrodes which are inserted into the soil, one of said electrodes typically being formed of copper, one being formed of a similar material to that used to form the pipeline and a standard electrode and are recorded and processed to provide a linear polarisation resistance (LPR) reading factorised with other measured soil parameters including redox.

In one embodiment the electrodes are inserted into the soil to a depth of at least 15 cm and are all located within the length of the portion of the pipeline.

In one embodiment, when there is a need to test the condition of the coating of the pipeline, the coating along and around the portion of the pipeline is exposed and the same is visually inspected with reference to a recording grid, each cell of the grid representing an identified location of the coating of said pipeline portion. An indication is then provided for each cell representing whether the coating in that cell is better than, worse than or similar to a datum which may, in one example, be the expected condition of the coating of the particular age on the particular pipeline type.

In addition, or alternatively, apparatus may be used to allow the condition of the coating to be analysed from above ground as an aid to selecting the optimum locations for pipeline inspection. In this case Pipe Current Mapper (PCM) apparatus may be used to pass a signal along the pipeline portion. If the signal is detected as having increased over a specific section along the pipe then this is an indication of the failure of the coating or the coating being poorer condition on that section as the coating is not masking the signal to the same extent as the reminder of the coating on the portion.

In one embodiment, in order to measure the condition of the pipeline wall, detection apparatus is moved along the portion and around the circumference of the said portion of pipeline so as to provide the measured readings as required. The measurement around the circumference of the pipeline is required as it is found that corrosion patterns can vary around the pipeline.

Typically the apparatus provides location data which indicates the particular location of the apparatus and hence the location of the readings which are being obtained at that time with respect to the pipeline portion.

Typically when the pipeline is steel or iron the apparatus includes a means for generating a magnetic flux, into the pipeline wall, means for monitoring the flux level and proximity sensing means. In one embodiment the apparatus includes means for providing azimuth data so as to determine the position of the apparatus around the pipeline circumference as well as along the length of the portion of the same.

Alternatively, if the pipeline is of a material with which ultrasonic or magnetic sensors cannot be used (such as concrete) a ground penetrating radar (GPR) device can be used to be placed onto the pipeline and provide data readings representative of the condition of the pipeline wall and in particular the degree and depth of pitting of the same. Typically a means for measuring the azimuth position will also be incorporated.

Typically to allow the prediction of leakage to be performed the detection of the condition of the pipeline portion is made with respect to assessing the level of the pitting of the pipeline wall. Once again the pipeline portion is represented as a grid of cells and a measurement of the degree of pitting is performed using the apparatus for each cell location and a value is provided. Typically, for each cell, the depth of the deepest pit is also measured and recorded.

In one embodiment this process is performed with respect to the deepest pit in each grid square which is, identified as depending from the outer wall of the pipeline inwardly and from the inner wall of the pipeline outwardly.

In one embodiment all other defects which are detected are ignored.

Typically this data is then processed to provide a predicted pattern of failure of the pipeline on an ongoing basis.

Typically the potential of structural failure of the pipeline portion is assessed with respect to individual defects and larger areas of pipe wall corrosion. In one embodiment this assessment is performed with reference to available data and measured data such as any or any combination of road and ground loading models, fracture potential of the pipeline, the soil analysis, temperature variations, measured current pipe wall thickness and/or the pitting measurements, and the condition of the pipeline coating if provided.

In one embodiment the length of the portion of the pipeline which is being measured can be selected to suit specific requirements. However it is found that a length of 1 meter can be sufficient for any given portion. In one embodiment a series of portions may be selected at spaced intervals long the length of the pipeline and each of these portions is measured in accordance with the method of the invention. In one embodiment the particular length of the portion of the pipeline and the measuring width of the apparatus are matched such that the apparatus as a whole does not need to be moved along the pipeline portion when measuring the portion and in this case the apparatus need only be moved around the pipeline portion circumference.

Typically when preparing the prediction of the pipeline condition based on the measured portions and/or determining maintenance requirements based on the predictions, suitable algorithms may be used into which the measured and predetermined data can be input as appropriate.

In one embodiment a database of data is prepared and generated on an ongoing basis. In one embodiment the database includes data from publicly available reference materials and/or data which is obtained from previously performed pipeline measurements. In one embodiment the data from previously performed measurements can be cross referenced with certain parameters such as soil type, geographical location, and/or depth of pipeline such that when subsequent reference is made to the data, the same can be assessed for suitability with respect to these characteristics in relation to the pipeline which is being assessed at that time.

In one embodiment the method includes the step of updating the database with measurement data from pipeline portions on an ongoing basis.

In accordance with the invention, by performing the measurement steps as herein indicated on portions of the pipeline, this measured data can be used in conjunction with known reference data to provide an accurate prediction of the condition of the remainder of the said length of pipeline. This prediction can then be used to determine whether the pipeline is in an acceptable condition at that time of measurement and also, if required, to provide an ongoing prediction of the condition of the pipeline over a time interval going forward. On the basis of these predictions remedial works can be scheduled for the pipeline thereby minimising the risk of potentially damaging and unexpected pipeline failure.

Typically the number of portions which are selected along the length of the pipeline are such as to ensure that at least minimum number of defects are identified so as to allow the subsequent assessment which is performed to be statistically valid. In one embodiment the number of defects required to be identified are 12 or more with respect to the monitoring of the pitting of the pipeline wall.

Typically each portion of the pipeline is represented by a grid and for each cell of the grid an assessment is made of the condition of the pipeline and a value is allocated. However it should be noted that for certain measurements such as, for example, measurement of the pitting of the pipeline wall, only one pit defect, typically the deepest, in each cell is counted as a defect, this is regardless of how many other pits may be located in that cell. This therefore means that when the minimum number of defects is being assessed only one defect per cell can be taken into account.

In one embodiment the size of the grid can be selected to represent a particular portion length and circumference of the pipeline in each instance.

Typically the prediction of failure of the pipeline at some stage in the future is undertaken using statistical analysis.

In a further aspect of the invention there is provided apparatus for the detection of at least one characteristic of a pipeline, said apparatus comprising a body including means for generating a magnetic flux along a portion of the pipeline wall, a means for detecting the magnetic field created and at least one proximity sensor wherein said apparatus includes means for generating an indication of whether any defects located arise on the internal or external wall of the pipeline.

In one embodiment azimuth data is generated to indicate the location of the apparatus with respect to the circumference.

Typically the apparatus is used to detect the presence of pitting depending inwardly from the external and/or internal walls of the pipeline. Typically the pipeline to be tested is formed of a metal.

In one embodiment the measuring apparatus is adapted to minimise the noise which may affect the monitoring. In one embodiment the electronic circuitry is provided on a single board in the body and/or the tyres on which the apparatus body is supported and movable are formed of low vibration material such as rubber or another similar material and/or magnetic detection means are used so as to reduce vibration.

In one embodiment the electronic circuitry is carried as a separate part to the monitoring apparatus body, thereby reducing noise and/or the physical size of the apparatus body which is required to be positioned at the pipeline thereby improving the accessibility of the apparatus.

In one embodiment data received from the apparatus on the pipeline is passed for analysis and plotting in real time.

In one embodiment the monitoring apparatus body placed at or adjacent to the pipeline is modular and can be increased or decreased in length and/or width so as to allow the same to be adapted for the specific monitoring to be performed.

In one embodiment an air gap is provided between the body, which carries the electromagnetic coils for generating the magnetic flux, and the pipeline being monitored. In one embodiment the air gap is crossed by a series of spaced conductive wires mounted in the body, said wires sufficiently flexible to flex when the apparatus is moved but also retain contact between the pipeline and apparatus body to allow the magnetic flux generated from the body into the pipeline to then pass along the wires which form the return path between the pipe and the body.

The provision of these wires typically allows a reduction in the number of coils which are required to be provided in the apparatus body to generate sufficient magnetic flux.

In one embodiment the wires are provided as a series of bristles, said bristles provided in spaced groups across the underside of the apparatus.

In one embodiment the body can be formed as a modular unit of, for example, first and second modules, with a first module being used alone for certain pipe monitoring requirements and, in other embodiments a second module can be placed on the first module to form the body. Typically each of the modules includes electromagnetic coils and so, where stronger magnetic flux is required to be generated, such as for larger pipelines, the two modules are used together in a stacked configuration.

In one embodiment the sensors used in the apparatus are bidirectional sensors, or alternatively tri-directional sensors.

Typically the apparatus includes one or more guide means which allow the guided movement of the body along the portion of the pipeline which is to be monitored. Typically, in addition further guide means are provided to allow the body to be moved circumferentially around the said pipeline portion.

In a further aspect of the invention there is provided apparatus for detecting the condition of a pipeline wall, said apparatus including a GPR device which is movable along the surface of the wall, said device transmitting signals which can be processed to indicate the depth of the wall surface with respect to a datum at each location.

In a yet further aspect of the invention there is provided a method of testing the condition of a pipeline, said method comprising the steps of determining a portion of the pipeline to be used as a sample to be tested, performing at least one test to determine a condition of the same wherein, if the number of defects detected is below a predetermined level, the condition of the pipeline is deemed to be acceptable and, if above the predetermined level, further testing of the pipeline is performed.

In one embodiment the defect data used includes a prediction of the depth of the defects in the pipeline wall.

Typically, if the condition of the pipeline is deemed to be acceptable, no further testing is performed.

In one embodiment the further testing is followed by statistical analysis of the test results.

In one embodiment the method includes the steps of assessing the condition of the soil and the corrosovity of the material from which the pipeline is formed and/or the condition of any coating of the pipeline.

Typically the analysis provides information relating to the current condition of the pipeline and also the future condition of the pipeline over a number of years.

In one embodiment structural defects of the pipeline can be assessed and selectively used as part of the pipeline condition analysis.

In one embodiment the average wall thickness is assessed.

In one embodiment the portion to be used as the test sample is selected randomly or alternatively, is selected as a portion which can be relatively easily accessed, such as the closest accessible point to a randomly selected location.

Typically all defects in the selected portion are recorded and those deemed not to be relevant are subsequently discarded.

In one embodiment the condition assessment of the pipeline is given for a predetermined length or the entire length of the pipeline.

In one embodiment the analysis includes a comparison of the predetermined loading values along the length of the pipeline and the predicted defects and the probability of the different conditions coinciding such as, for example, high loading occurring at the same location as a high level of defects which would further increase the risk of failure.

Specific embodiments of the invention are now described with reference to the accompanying drawings wherein.

Figure 1:
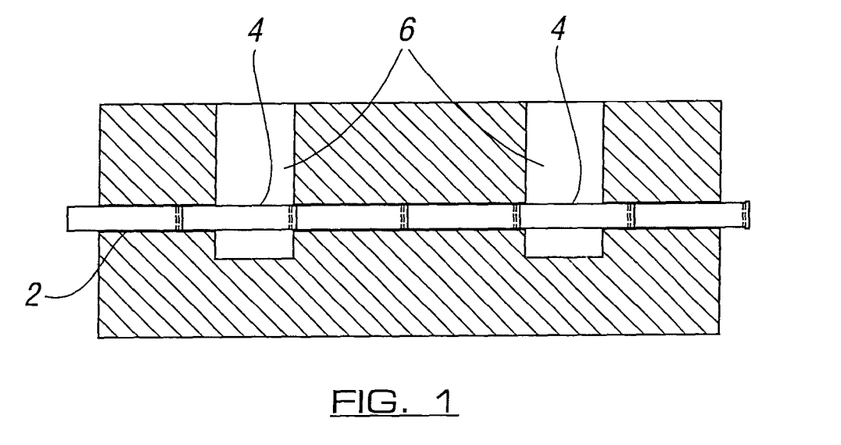
FIG. 1 illustrates a length of pipeline which can be assessed in accordance with the invention.

Referring firstly to FIG. 1 there is illustrated a length of pipeline 2 which is to be assessed and for which a prediction of its condition is to be determined.

The pipeline can be of a number of kilometers in length and in accordance with the invention at least one, and in the example shown two, portions 4 of the pipeline are selected to be measured. The portions which are selected may be selected to be at a location which is identified as being most prone to corrosion and therefore can be said to be most likely to be in the worst condition along the length of the pipeline or may be at locations where the maximum of the combined loading regimes are being applied or may be randomly selected to be representative of the deterioration of the length of pipeline.

Figure 2:
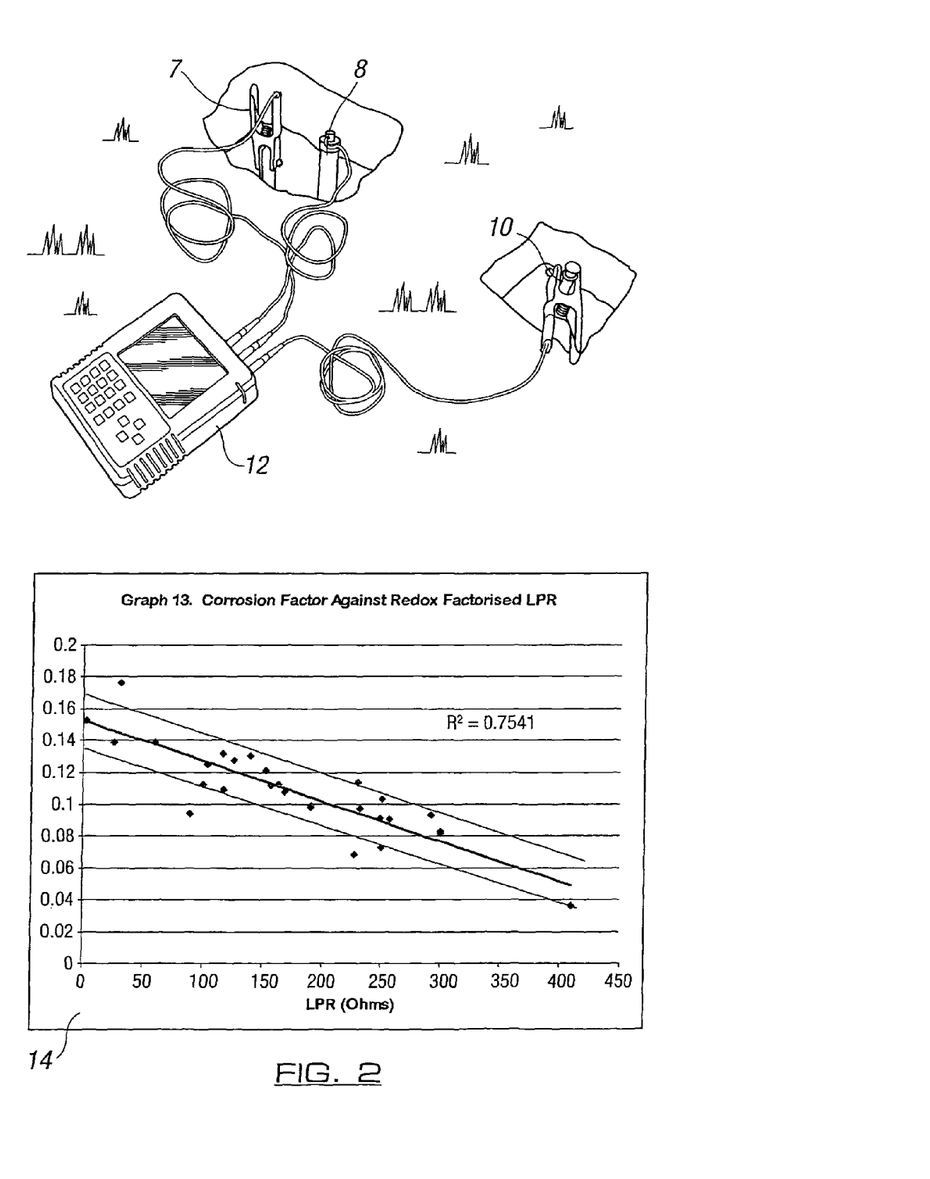
FIG. 2 illustrates one possible form of apparatus for assessing soil conditions in the vicinity of the portion of pipeline being measured.

With the portion to be measured having been determined, then in accordance with the invention the condition of the soil 6 in the vicinity of the pipeline portion 4 is required to be assessed. In one embodiment this can be achieved by using the apparatus as shown in FIG. 2 in which electrodes 7, 8, 10 are placed into the soil above the portion of the pipe. Typically, one of the electrodes is of copper, one of the electrodes is of the same material as the pipe walls and the other electrode is of a standard selected material. The electrodes are connected to a processing device 12 and the data received is used to generate a graphical representation 14 as shown in FIG. 2 which is representative of a Redox Factorised linear polarisation resistance (LPR). This can be repeated for each of the measured portions of the pipeline to determine whether the soil type is the same at each portion location or not.

Other soil condition factors such as pH, ground type, moisture content and heterogeneity may also be measured and taken into account to give an indication of the soil type.

Most pipelines include a coating material on the external surface of the same in order to try and protect the pipeline wall from corrosion and the condition of this coating (if provided) is assessed in accordance with the invention.

Figure 3A:
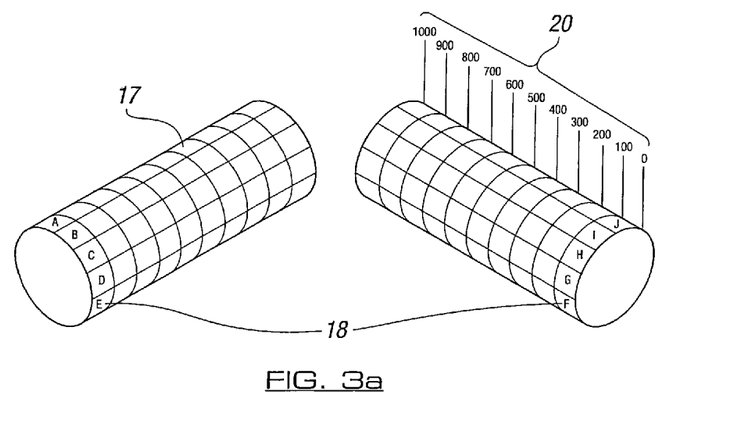
FIGS. 3a and b illustrates the method followed in assessing the condition of the coating of said pipeline portion.
Figure 3B:
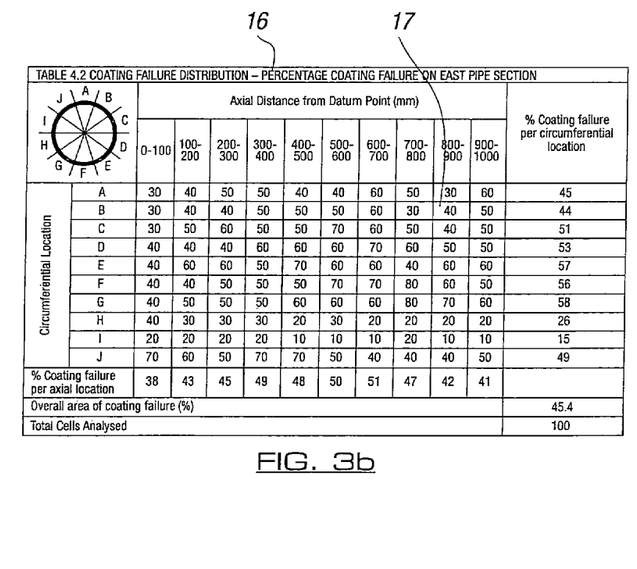

In accordance with the embodiment shown in FIG. 3 this is achieved by exposing the coating around the periphery of and along the length of the portions 4 of the pipeline and performing a visual check. The pipeline portion is represented by a grid 16 and FIG. 3*a* illustrates how this grid effectively is mapped around the periphery of the coating of the pipeline portion 4. Each cell 17 of the grid 16 is provided with a coordinate 18 relating to the position round the circumference of the pipeline and a coordinate 20 relating to the position along the length of the pipeline. For example the cell 17 shown by the reference arrows has the co-ordinates B800-900 on the grid 16. The size of the grid can be selected to suit the pipeline in question as can the size of area of the pipeline represented by each of the cells. In one embodiment the width of the portion is equivalent to the length of pipeline which can be measured by monitoring apparatus without having to move the apparatus as a whole along the pipeline portion.

For each cell 17 a value is allocated to the percentage of the coating failure at that cell location. This value may in one embodiment be with respect to the range of no coating to full coating or alternatively may be with respect to an "average" coating value. The values are then assessed and the areas with the coating condition below a certain level can be identified in this case by darker shading of the cells.

In addition, or alternatively to the above, a PCM signal may be transmitted along the pipeline portion and detection means are mounted externally of the pipeline to identify the same. Typically the provision of the coating will act to mask or damp the signal to a reduced strength when detected externally of the pipeline. However if the coating is removed or thinner at any location on the portion the signal will be detected as having a greater strength thereby indicating the poor condition of the coating at that location. Thus in accordance with this embodiment the grid cells can again be filled with a reading indicative of the condition of the coating at that cell but the reading can be obtained from a position above ground via the signal detection means thereby avoiding the need for the pipeline portion to be available for a visual inspection.

Figure 4:
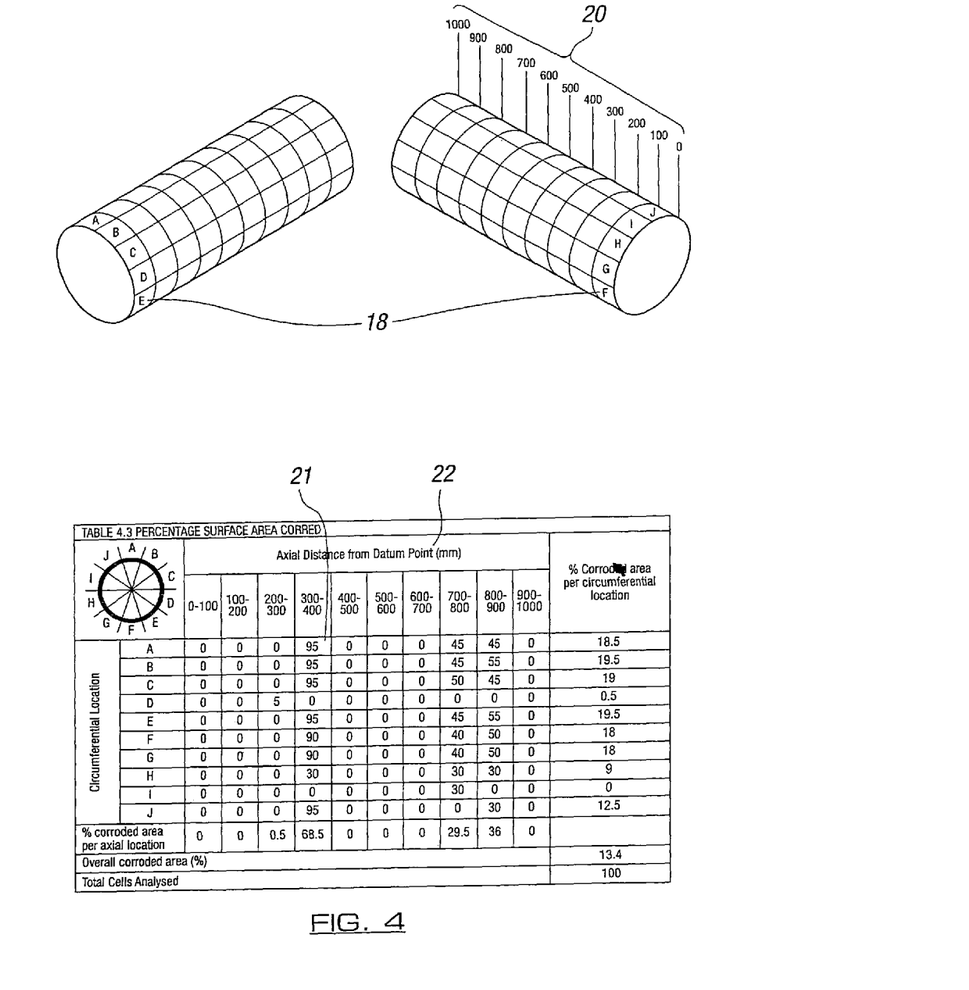
FIG. 4 illustrates the method followed in assessing the condition of the pipeline wall.

In accordance with the invention the condition of the pipeline wall is assessed with reference to the pitting of the wall. The assessment may be made with regard to the occurrence of pitting regardless of whether the same depend from the external or internal surface of the pipeline wall, or, alternatively the location of the pitting with respect to the internal or external surfaces can also be identified. In either case the assessment is performed along the length of the portion and also around the circumference of the portion of the pipeline portion. The data indicative of the pitting is logged and mapped onto a grid 20 with a series of cells 21 with coordinates so that the location of the pitting is mapped to a specific location on the pipeline portion. An example of the grid 22 is provided in FIG. 4 with each of the cells 21 having a corrosion value allocated thereto. Once more the grid is mapped to the pipeline portion 4 in a similar manner and with the same co-ordinates as indicated in FIG. 3*a*.

It is also possible, in one embodiment, for the loading characteristics of the length of pipeline to be determined and this information to be used in conjunction with results obtained for the inspection for defects. For example, if, on the basis of this analysis it is determined that a location of high loading somewhere along the pipeline will coincide with a predicted location of high defects then this will be highlighted and may result in remedial work being required to be performed immediately or at least earlier in a schedule of repairs than would otherwise have been envisaged. The same applies to a location on the pipeline wherein the loading is relatively low in which case predicted defects at that location are given less significance in the overall analysis and prediction of the pipeline condition.

In whichever embodiment it is desired that the circumference of the pipeline portion needs to be inspected. The number of portions which are inspected along the length of the pipeline is typically influenced by the need to identify and measure at least a minimum number of statistically valid number of pitting occurrences. For each cell where there is pitting only one pitting occurrence in that cell counts as a defect.

When the pipeline material is metallic, the monitoring apparatus used comprises means for emitting a magnetic flux or field. The magnetic flux is induced by the conductor apparatus 24 which has a body 40 which causes generation and movement of the magnetic flux from the body into the pipeline wall 4 and to return to the body 40. When the interior and exterior surfaces of the pipeline are smooth, and generally fault free the return magnetic flux level is similar to that sent from the body to the pipeline but the location of a defect such as pitting, causes leakage of magnetic flux through the pipeline wall and the change in magnetic flux is monitored by monitoring means which can be provided on the body and connected to processing means which can also be provided on the body or connected thereto and carried separately so as to minimise the size of the body and minimise vibration.

Figure 5A:
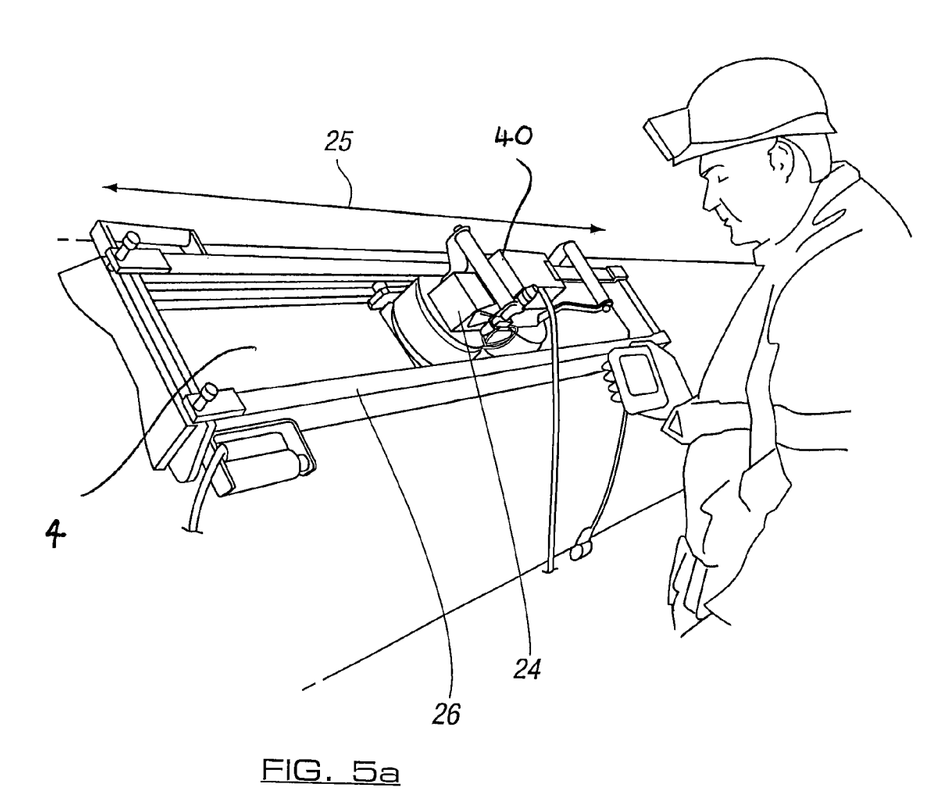
FIG. 5a-c illustrate embodiments of the apparatus which may be used to perform the measurements required for FIG. 4.

The apparatus body is fitted with wheels and, if required, a suspension system, that serve to facilitate movement of the apparatus along the pipe section 25 being inspected, and to maintain an air gap 44 between the pipeline wall and the underside of the body. This system allows adjustments to be made in order to accommodate variations in pipe geometry. The apparatus body 40 is typically located on guide means in the form of a frame and one example of the same is provided in FIG. 5*a*. As shown in FIG. 5*a* the detecting head 24 is capable of moving in the direction of arrow 25 along the length of the frame 26 and the frame itself is capable of being moved around the circumference of the pipeline wall 4, possibly on further guide means (not shown) so that it will be appreciated that the entire portion of the pipeline can be in terms of length of the same and circumference of the same assuming access is possible.

Proximity sensors are also provided in the body 40 which are sensitive to the presence of the pipe material beneath it. When passing along a pipe showing no or insignificant corrosion a constant output signal in terms of volts would be expected to be received from the proximity sensors. However, if a change in condition is detected on or near the external surface of the pipeline the proximity sensor reading will change.

The detector array is moved by pulling it by hand, along the guide means, thus scanning the pipe section below it. The guide means and body thereon can then be moved in stages circumferentially around the pipe to allow adjacent pipe lengths to be inspected. This process continues until preferably the entire pipe circumference has been inspected.

Figure 5B:
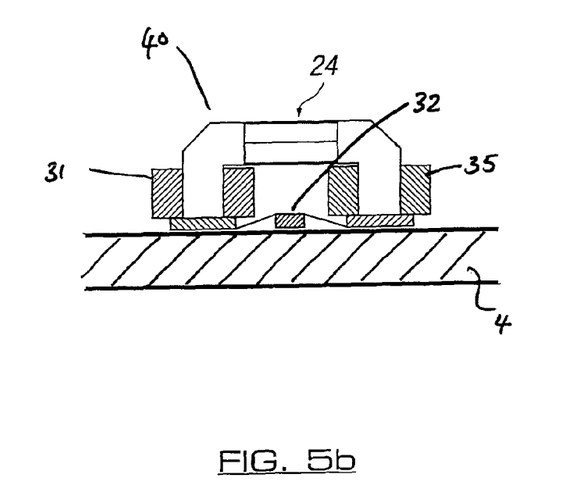

The body typically consists of two electromagnets 31, 35 which are located on the body to provide a return magnetic flux path between them and through the pipeline wall 4. When this assembly is placed on the track above the pipe being inspected the pipe structure provides the final element in the magnetic flux flow path.

In one embodiment the body further includes magnetic flux leakage monitors 32 in the form of Hall effect sensors fixed into the body along with proximity sensors. The body is also fitted with a means of recording its position relative to the guide means and hence in relation to the pipe section 4 being scanned.

When the body 40 is passed along the portion, if the proximity sensors show no or insignificant corrosion a constant output signal is generated to be received from the proximity sensors. However the proximity sensors can detect the interface between, for example, a graphite layer and the original pipe material of a cast iron pipe and register the change by the change in received voltage as the body passes over the corroded area if that area is at or near the external surface of the pipeline. However, the proximity sensors do not react in this way when moving over an area of the pipe with corrosion at or near the internal wall of the pipeline as the proximity sensor is set so as not to detect through the depth of the pipe wall. In this way the detector array can detect and distinguish between external and internal corrosion, as firstly the magnetic flux detection detects corrosion at any position in the pipeline wall and the proximity sensor only reacts if the corrosion is at or near the external surface of the pipeline.

The strength of the detected magnetic flux or field is used to determine the presence of pitting in the pipeline wall and the one or more proximity sensors allow the determination of whether the pitting is present in the internal or external surface of the pipeline wall.

Figure 5C:
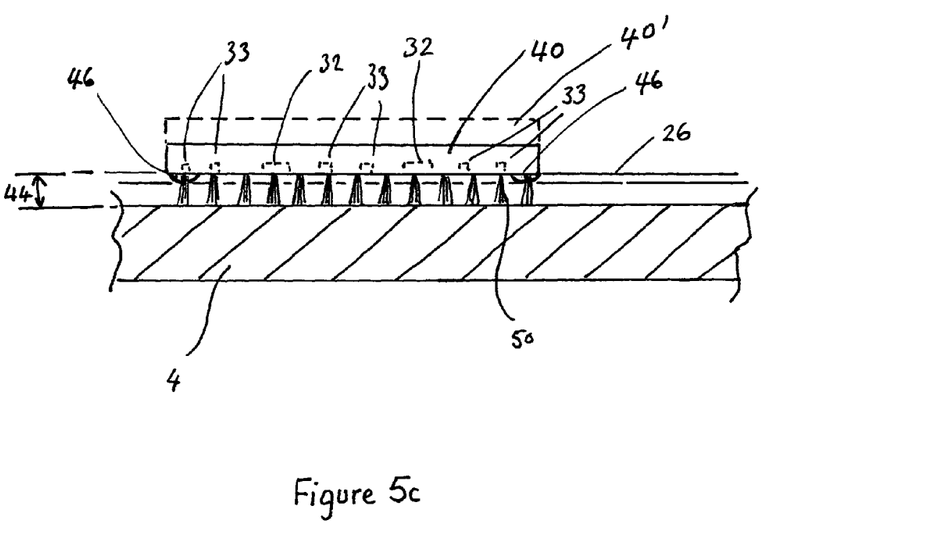

FIG. 5*c* illustrates a further embodiment of apparatus which can be used. Where appropriate the same reference numerals are used for the same components. In this case the body 40 of the apparatus is provided to run along the length of track to be tested along guide means 26, with handles (not shown) typically being provided to allow the body to be manually moved. Wheels 46 are provided on the body to engage and move along the guide means, with the wheels being formed of a material to minimise vibration as the same move along the track. The body 40 in this case is shown formed of one modular unit, but, if required to generate a stronger magnetic flux to inspect or monitor the pipeline wall, for example a pipeline wall 4 of greater depth, a second modular unit 40', shown in broken lines, can be attached to the first modular unit and electrically connected, typically in a stacked configuration. The body 40 also includes hall effect sensors 32 and proximity sensors mounted therein and it should be appreciated that the particular configuration of the same will be selected to suit specific requirements.

An air gap 44 is provided between the underside of the body and the external wall of the pipeline. The apparatus can be used with the air gap or, as shown in this embodiment, the air gap can be bridged by groups of wires or bristles 50 which are mounted on the underside of the body and the free ends of the same contact with the pipeline wall as shown. It is found that the spaced array of groups of bristles or wires allows the number of coils of the electromagnets to be reduced and generally provides a more reliable monitoring performance as the magnetic flux can be carried along the conducting wires particularly from the pipeline to the body to allow the return magnetic flux to be monitored by sensors 32.

Typically the bristles or wires are sufficiently flexible to allow the same to flex when the body is moved while at the same time being sufficiently rigid so as to maintain the contact between the pipeline and the body.

Figure 6:
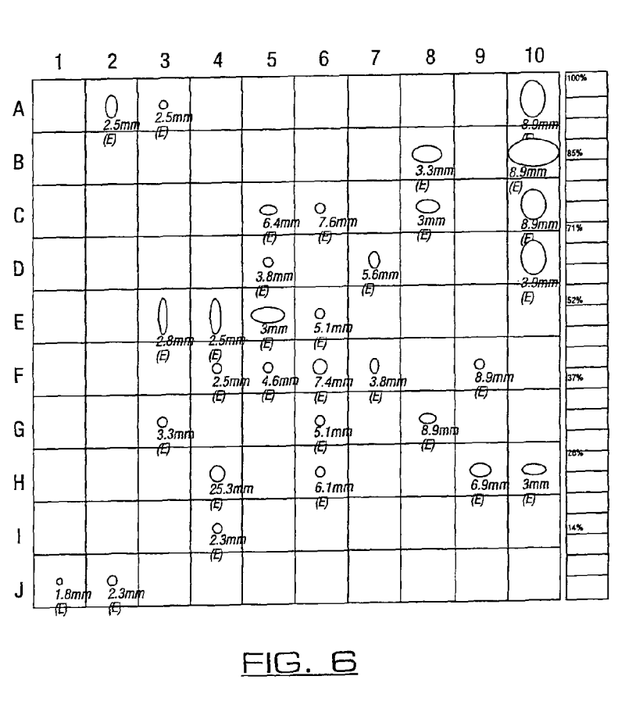
FIG. 6 illustrates a grid of results obtained using the apparatus of FIG. 5a-c.

In addition to detecting the presence of pitting, the depth of at least the deepest pit in each cell is determined and mapped onto a grid as shown in FIG. 6. Thus, the frequency and spread of the pitting is identified and also those areas where the pitting is deepest, and hence the pipe wall thinnest, are identified.

In certain cases the material from which the pipeline wall is formed prevents the uses of the magnetic field detection means. In this case alternative apparatus in the form of a GPR device can be used. The GPR device can be used in a similar manner to that described above with the detection head being moved along and around the portion so as to allow indicative readings to be obtained.

With this measurement data available, the same can then be graphically represented and processed such that, for example, data relating to the current deepest pitting and number of critical defects can be used to provide predicted values for the future defects and future critical defect patterns.

These predictions can be made by using statistical analysis, typically utilising suitable algorithms into which the measured data can be input as appropriate. In addition to the measured data other reference data and/or data from previous pipeline measurements which are applicable to the current pipeline being measured may be selectively obtained from a reference database and used as required in the algorithms in order to provide an accurate and reliable prediction for the whole of the pipeline length to which the assessment is being applied rather than just the portions which have been measured.

Other predictions which may be provided include predicted internal and external pipeline wall defect patterns over the defined length of pipeline as the likely ongoing corrosion rate can be calculated with reference to the measured data and known reference data. The predicted year of structural failure may also be provided with reference to the measured wall thickness and calculated critical wall defects and other reference data such as the maximum loading regime on the pipeline. Predictions of the effect of reducing or increasing the combined loading regimes on the year of failure can also be made.

It will therefore be appreciated that the current invention provides apparatus and a method which allows the scanning of the condition of at least one portion of pipeline to be performed in an efficient and reliable manner, and as a result the measured data can be used to provide an accurate indication of the condition of a length of the pipeline in which the said at least one portion is located.

The invention claimed is:

1. A method for detecting a condition of a pipeline along a length of the pipeline, said method comprising the steps of:
   identifying at least one portion which is to be tested along the length of the pipeline;
   measuring for said at least one portion a condition of a pipe wall using a pipeline wall condition detection apparatus to measure defects;
   measuring a condition of a protective coating, if one is provided, on said at least one portion;
   representing said at least one portion as a grid of cells, the grid being selected to represent a particular length and circumference of the pipeline;
   assessing a level of pitting in at least one of the cells and providing a value of a depth of a measured pit in at least one of the cells;
   assessing the condition of the protective coating, if one is provided, by allocating a value to a percentage of coating failure at the at least one cell;
   determining characteristics of soil in a vicinity of the at least one portion by measuring one or more parameters of a soil condition and processing the measured one or more parameters to generate a representative soil type;
   repeating the assessment steps of the level of the pitting and the condition of the protective coating, if one is provided, for at least one further cell in the grid; and utilizing measurement information gathered in the aforementioned steps to provide an indication of the condition of the pipe wall and the condition of the protective coating, if one is provided, along the length of the pipeline and the soil condition along the length of the pipeline based on the measurements taken with respect to said at least one portion.

2. The method according to claim 1, wherein based on one or more of the accurate indication of the conditions along the length of the pipeline, performing or scheduling any required remedial actions on the pipeline scheduled for future performance.

3. The method according to claim 1 wherein the at least one portion is that which is located in a critical part of the pipeline and/or located in a part of the pipeline which is regarded as being most susceptible to deterioration and/or most heavily loaded.

4. The method according to claim 1 including randomly selecting portions to be tested along the length of the pipeline.

5. The method according to claim 1 wherein the one or more parameters of the soil condition is at least one selected from the group consisting of: pH, resistivity, redox potential, ground type, moisture content and heterogeneity of the soil.

6. The method according to claim 1 wherein the soil condition is determined by using apparatus according to the following steps:
   inserting a plurality of electrodes into the soil, one of said electrodes typically being formed of copper, one being formed of a similar material to that used to form the pipeline and a further electrode; and
   recording data from the same and processing to provide a linear polarization resistance reading which is factorized with other measured soil parameters.

7. The method according to claim 1 further including the steps of:
   exposing the protective coating, along and around the at least one portion; and
   visually inspecting the protective coating with reference to a recording grid, each cell of the recording grid representing an identified location of the protective coating of said at least one portion and an indication is provided for each cell to represent whether the protective coating at that cell location is better than, worse than or similar to a predetermined datum condition.

8. The method according to claim 1 wherein a pipe current mapper apparatus is used to pass a signal along the at least one portion and if the signal is detected as having increased over a specific length of the pipeline this is an indication of the failure of the protective coating or the protective coating being in a poorer condition on that specific length of the pipeline.

9. The method according to claim 1 wherein the pipeline wall condition detection apparatus is used to provide the measured readings of the pipe wall both along the length of the at least one portion and around the circumference of said at least one portion.

10. The method according to claim 9 providing location data which indicates a particular location of the pipeline wall condition detection apparatus and hence a location of readings with are being obtained at that time which respect to the said at least one portion.

11. The method according to claim 9 including the steps of generating a magnetic flux into the pipe wall if the pipeline is formed of metal, monitoring the flux level, and proximity sensing.

12. The method according to claim 1 including recording the deepest pits in each cell which depend from an outer wall of the pipeline inwardly and from an inner wall of the pipeline outwardly.

13. The method according to claim 12 including ignoring any other pits or any defects which are detected.

14. The method according to claim 1 including preparing a database of data and generating on an ongoing basis said database including data from publicly available reference materials and/or data which is obtained from previously performed pipeline measurements.

15. The method according to claim 14 including cross referencing the data from previously performed pipeline measurements with certain parameters of any or any combination of soil type, geographical location, and/or depth of pipeline and when subsequent reference is made to the data, the same can be assessed for suitability with respect to these characteristics in relation to the pipeline which is being assessed at that time.

* * * * *